(12) United States Patent
Oliver (10) Patent No.: US 8,182,488 B2
(45) Date of Patent: May 22, 2012

(54) APPARATUS AND METHOD FOR IMPLEMENTING PATELLA RESECTION GUIDE DURING MINIMALLY INVASIVE SURGERY

(76) Inventor: Ralph Scott Oliver, Duxbury, MA (US)

( * ) Notice: Subject to any disclaimer, the term of this patent is extended or adjusted under 35 U.S.C. 154(b) by 1375 days.

(21) Appl. No.: 11/717,841

(22) Filed: Mar. 14, 2007

(65) Prior Publication Data

US 2007/0233142 A1    Oct. 4, 2007

Related U.S. Application Data

(60) Provisional application No. 60/782,159, filed on Mar. 14, 2006.

(51) Int. Cl.
*A61F 5/00* (2006.01)
(52) U.S. Cl. ......................................................... 606/87
(58) Field of Classification Search ................ 606/86 R, 606/87, 88
See application file for complete search history.

(56) References Cited

U.S. PATENT DOCUMENTS

| | | | |
|---|---|---|---|
| 2,530,203 A * | 11/1950 | Lear ............................. | 269/280 |
| 5,021,055 A | 6/1991 | Burkinshaw et al. | |
| 5,129,907 A | 7/1992 | Heldreth | |
| 5,536,271 A * | 7/1996 | Daly et al. ..................... | 606/80 |
| 5,542,947 A | 8/1996 | Treacy | |
| 5,575,793 A * | 11/1996 | Carls et al. ..................... | 606/80 |
| 5,667,512 A | 9/1997 | Johnson | |
| 6,056,754 A | 5/2000 | Haines et al. | |
| 6,702,821 B2 | 3/2004 | Bonutti | |
| 7,632,279 B2 * | 12/2009 | Bastian .......................... | 606/88 |

OTHER PUBLICATIONS

International Search Report for International Application # PCT/US07/06389.

* cited by examiner

*Primary Examiner* — Anu Ramana
(74) *Attorney, Agent, or Firm* — Burns & Levinson LLP; Jacob N. Erlich, Esq.; Marlo Schepper Grolnic (57) ABSTRACT

An improved patella resection guide and a method for applying the patella resection guide during the performance of knee arthroplasty. The patella resection guide includes a plurality of gripping handles having a corresponding plurality of pivotally interconnected crossover members at distal ends of said gripping handles, an opening in each pivotally interconnecting crossover member wherein one crossover member is position inside another crossover member, a stem having a proximal end connected to each gripping handle and each pivotally interconnected crossover member wherein the members are intertwined at a crossing point and are adjoined by fastening means to said stem, and further having a distal end comprised of a female receptor, a clamp having a top flange and side flange, and adjustable locking means for fixing a distance between the teeth of the top flange.

29 Claims, 10 Drawing Sheets

APPARATUS AND METHOD FOR IMPLEMENTING PATELLA RESECTION GUIDE DURING MINIMALLY INVASIVE SURGERY

CROSS-REFERENCE TO RELATED APPLICATIONS

This application claims priority to and benefit of U.S. Provisional Patent Application Ser. No. 60/782,159 filed Mar. 14, 2006 and entitled PATELLA RESECTOR.

FIELD OF THE INVENTION

The invention relates to an improved patella resection guide and a method of implementing the patella resection guide during the performance of knee arthroplasty.

BACKGROUND OF THE INVENTION

Total knee replacement is presently an accepted medical treatment for arthritic knee pain that has failed or been unresponsive to conservative management. Over the past few decades, the surgical technique has continuously evolved. Recently, new minimally invasive surgery (MIS) techniques have demonstrated benefits to the surgical patient with faster rehabilitation and potential for less morbidity. These new techniques require new instruments because of the limited exposure of the anatomy.

Traditional total knee replacement surgery requires a wide exposure with an incision of 8-10 inches. The joint surfaces of the femur and the tibia, and frequently the patella, are replaced with metal and polyethylene components. In this approach, a lengthy extensile exposure is achieved by a long incision that extends through the quadriceps muscle and the patella is completely inverted 180 degrees so that the undersurface of the patella is directly facing the surgeon. Frequently, the patella demonstrates significant arthritic wear and requires replacement. The patella is a very irregular bone, and with arthritis the wear creates further unevenness. Various patella resection guides (jigs) have been designed to assist the surgeon in the removal of the patella undersurface. The resection guides allow the surgeon an opportunity to review the planned resection. The guide is carefully placed into position and firmly clamped into position.

Surgeons sometimes use a freehand technique which may leave the cut surface with significant irregularities that would be potentially detrimental to the final resurfacing. It is very necessary that the patella resection guide not become dislodged during the process of patella resection because an irregular surface may result Minimally invasive surgery (MIS) now appears to be the next step in the evolution of total knee arthroplasty. This technique utilizes a 10-12 cm (4-5 inch) incision along the medial border of the patella. A small incision of 2-3 centimeters is used to release the medial muscle, the vastus medialis obliques, one of the four muscles that are part of the quadriceps musculature that control the patella. The patella is next inverted only 90 degrees and is evaluated by the surgeon on end, with the lateral patella placed on the femur. Current patella resection guides are bulky and are difficult to grasp the patella in this 90 degree position.

There are always new breakthroughs in medicine. MIS is now here and is being further refined by the many innovative orthopedic surgeons around the world. Furthermore, to assist in the limited exposure allowed with the MIS approach, computer navigation of the knee has greatly provided the surgeon important information for neutral alignment of the total knee components for the potential of a longer lasting result. New techniques will require new instruments. The inventive patella resection guide and method of applying said patella resection guide in a surgical procedure as described herein is one of the instruments that will be necessary as knee surgery continues to evolve.

SUMMARY OF THE INVENTION

According to an aspect of the present invention, a patella resection guide for minimally invasive surgery is provided, said patella resection guide comprising a plurality of gripping handles having a corresponding plurality of pivotally interconnected crossover members at distal ends of said gripping handles, an opening in each pivotally interconnecting crossover member wherein one crossover member is position inside another crossover member, a stem having a proximal end connected to each gripping handle and each pivotally interconnected crossover member wherein the members are intertwined at a crossing point and are adjoined by fastening means to said stem, and further having a distal end comprised of a female receptor, a clamp having a top flange and side flange wherein the female receptor on the distal end of the stem receives the side flange, and further wherein the top flange comprises teeth for gripping a patient's patella; and adjustable locking means for fixing a distance between the teeth of the top flange.

According to a second aspect of the present invention a method for applying a patella resection guide for minimally invasive surgery is provided, A method for resecting a patella in minimally invasive surgery, said method comprising surgically exposing the patella and adjacent ligament and tendon structures; providing a patella resection guide having a plurality of gripping handles having a corresponding plurality of pivotally interconnected crossover members at distal ends of said gripping handles, an opening in each pivotally interconnecting crossover member wherein one crossover member is position inside another crossover member, a stem having a proximal end connected to each gripping handle and each pivotally interconnected crossover member wherein the members are intertwined at a crossing point and are adjoined by fastening means to said stem, and further having a distal end comprised of a female receptor, a clamp having a top flange and side flange wherein the female receptor on the distal end of the stem receives the side flange and further wherein the top flange comprises teeth for gripping a patient's patella, and adjustable locking means for fixing a distance between the teeth of the top flange; engaging adjustable locking means; and rotating patella such that said clamp is at an approximate right angle to the gripping handles of the patella resection guide.

According to a third aspect of the present invention a patella resection guide for minimally invasive surgery is provided, said patella section guide comprising a plurality of gripping handles; a plurality of pivotally interconnected crossover members adjoined to said plurality of gripping handles; a stem connected to each gripping handle and each pivotally interconnected crossover member wherein the members are intertwined at a crossing point and are adjoined by fastening means to said stem; a clamp having a top flange and side flange, wherein the stem is further adjoined by fastening means to said side flange, and the top flange comprises teeth for gripping a patient's patella; and adjustable locking means for fixing the top flange to the top surface of the patella.

According to a fourth aspect of the present invention, a method for resecting a patella in minimally invasive surgery is provided, said method comprising surgically exposing a top surface of a patella of a patient's knee for application of a patella resection guide; applying a top flange of a patella resection guide clamp having a top flange and a side flange to the patella, wherein said patella resection guide comprises a plurality of gripping handles for positioning said clamp, a plurality of pivotally interconnected crossover members, a stem connected to each gripping handle and each pivotally interconnected crossover members wherein the members are adjoined by fastening means to said stem and wherein said stem is further adjoined by fastening means to said clamp, and adjustable locking means for fixing said clamp on the top surface of the patella; engaging adjustable locking means; and rotating patella such that said clamp is at an approximate right angle to the gripping handles of the patella resection guide.

It is an object of the present invention to reduce the angle of patella inversion required during knee replacement surgery.

It is an object of the present invention to provide a significantly reduced incision site in accordance with minimally invasive surgery.

DETAILED DESCRIPTION OF THE PREFERRED EMBODIMENT

Figure 1:
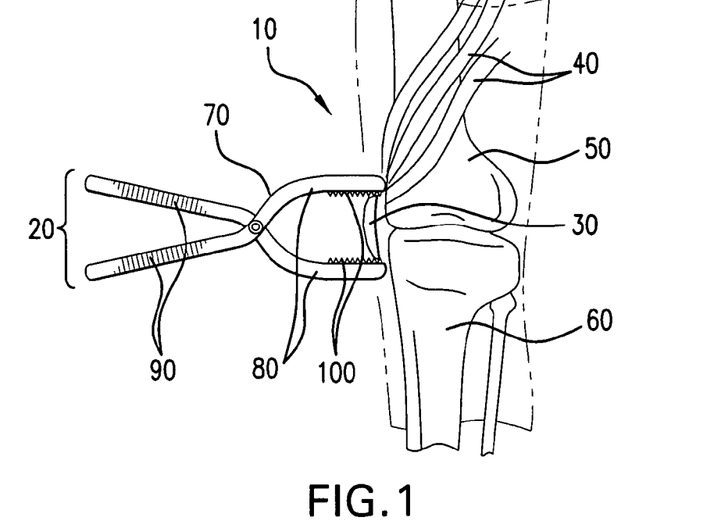
FIG. 1 is a pictorial of a traditional resection guide as applied to a patient's right knee.

With reference first to FIG. 1, a free hand drawing of a traditional patella resection guide 20 is depicted as applied to a patient's right knee 10. The quadriceps 40, femur 50, and tibia 60 surrounding the right knee 10 are also illustrated herein. Resection guide 20 comprises a cradle 70 having a pair of gripping elements 80, and a pair of handles 90. The gripping elements are furnished with teeth 100 and are shown in FIG. 1 as specifically applied to the patella 30 of the knee 10. It is well known in the art that resection guides have a row of teeth on either side to allow firm fixation of the guide onto the patella, superiorly and inferiorly. FIG. 1 depicts the patella as it is inverted 180 degrees such that the undersurface of the patella is directly viewable.

Following the resection, the new patella surface is reviewed for "flatness", to ensure there is an equal amount of bone removed from both the medial and lateral facets and also the equality of bone resection superiorly and inferiorly. At this point, drill holes are inserted and final patella cementing can be achieved with firm fixation of the polyethylene patella component.

Figure 2:
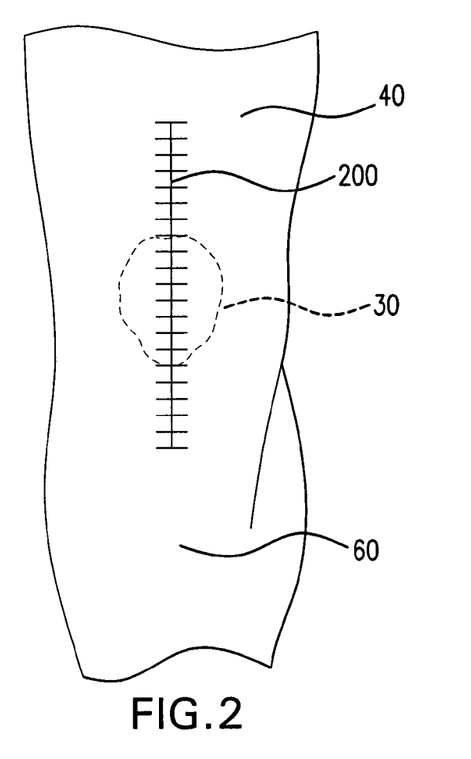
FIG. 2 is a pictorial of an exemplary illustration of an incision path when implementing a guide as set forth in FIG. 1.

Once the patella is cemented and fixed, the incision may be closed. Due to the 180 degree inversion of the patella during surgery using a traditional resection guide, a wide and unsightly incision path is created. FIG. 2 depicts the corresponding path of the incision when using a traditional guide. In this instance, a traditional incision path 200 may extend from the quadriceps 40, through the patella 30, to the tibia 60 as shown.

The innovative patella resection guide or patella resector in accordance with the present invention is designed at a right angle such that during implementation, the surgeon is able to visualize the entire patella with the guide to the side. As such, the guide and resected patella are not interfering with the surgeon's visibility of the undersurface of the patella and the ligaments and tendons of the knee. The smaller incision desired make visualization of the bone and soft tissues difficult and it is important to utilize these instruments to allow for this downsized incision. The "teeth" of the resection guide are applied to the superior and inferior patella, and firmly ratcheted into position. The patella resection is completed with full exposure of the patella. The new patella surface is reviewed and further fine resection is sometimes necessary for the finished result. Patella cementing techniques may be used as in the standard approach.

Figure 3:
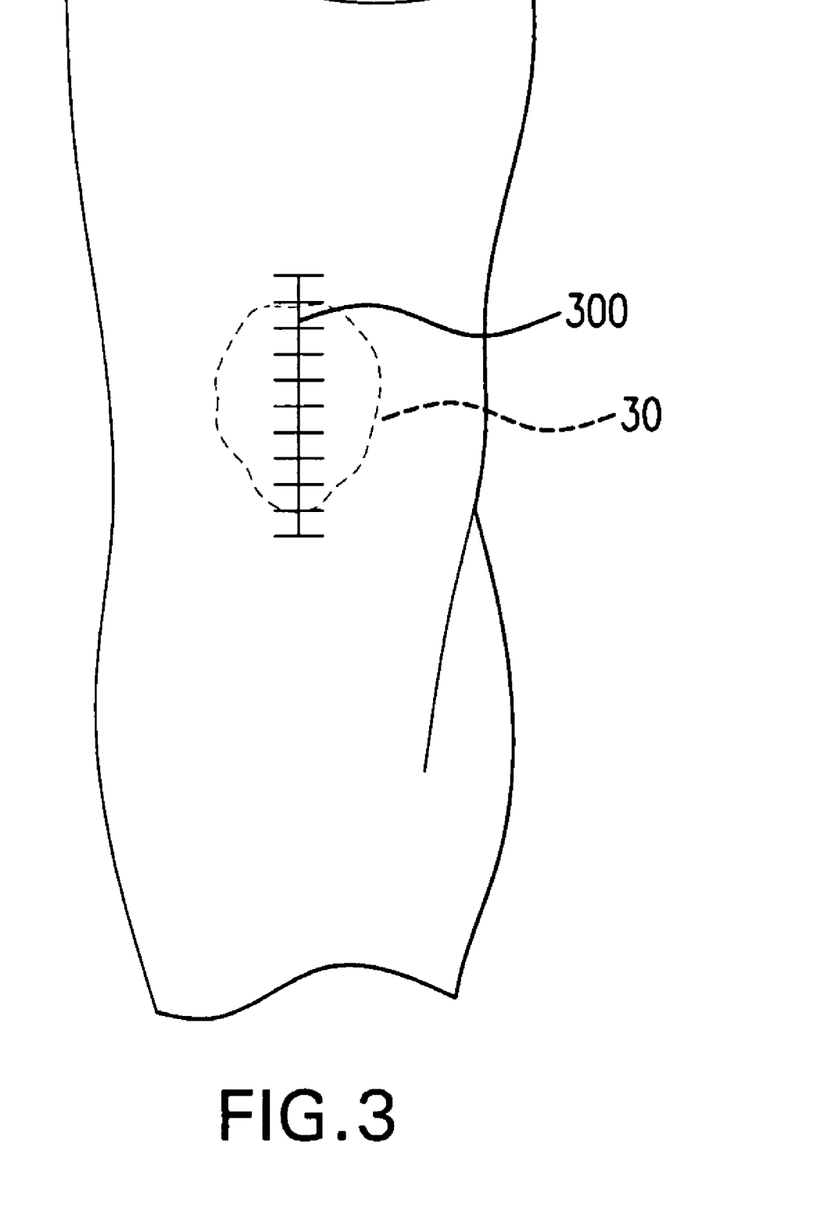
FIG. 3 is a pictorial of an incision path exemplary of that used in accordance with the present invention.
Figure 4:
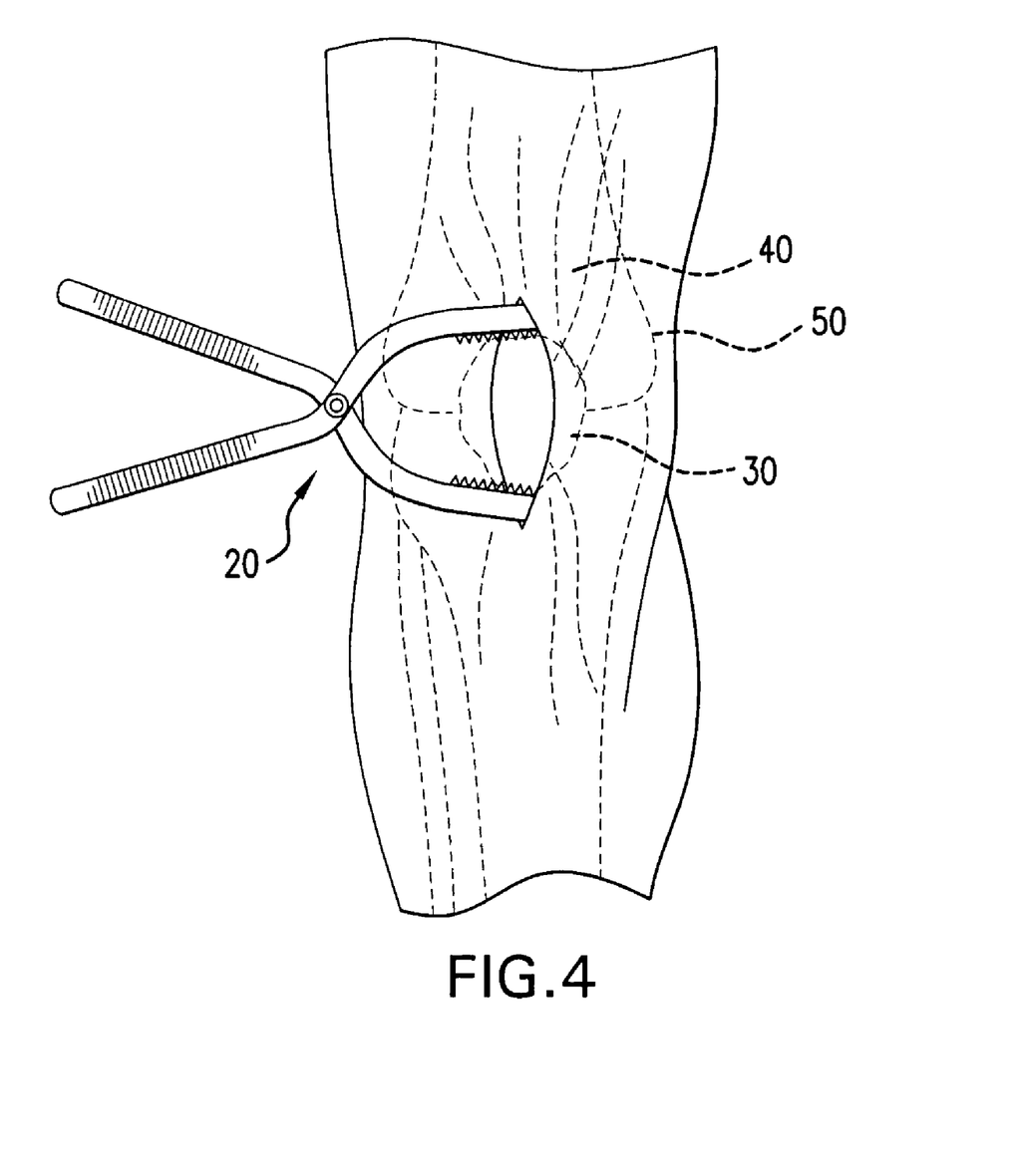
FIG. 4 is a pictorial of a patella resector in accordance with the present invention as it may be placed on a patient's right knee.

FIG. 3 demonstrates an incision path 300 as used in the minimally invasive surgery described herein. It is noted that the incision path 300 barely extends past the patella 30. FIG. 4 correspondingly depicts a pictorial of the placement of the traditional bulky patella resector at a right angle on a patient's right knee. It is observed that the line of visibility to the underside of the patella and knee components is obstructed by the bulky guide. FIGS. 5 through 10 show top, end, and lateral views of a traditional patella resection guide and the resector of the present invention.

Figure 5:
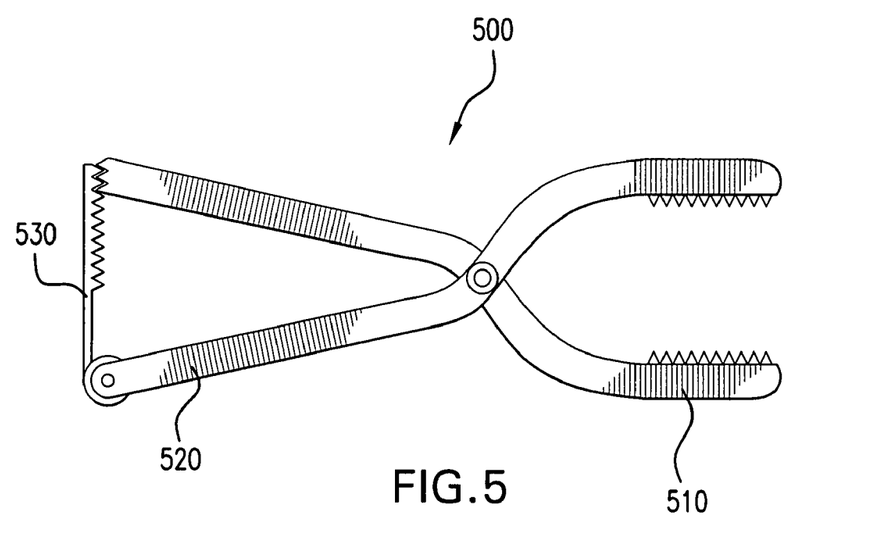
FIG. 5 is a pictorial of a top view of a traditional resection guide.
Figure 6:
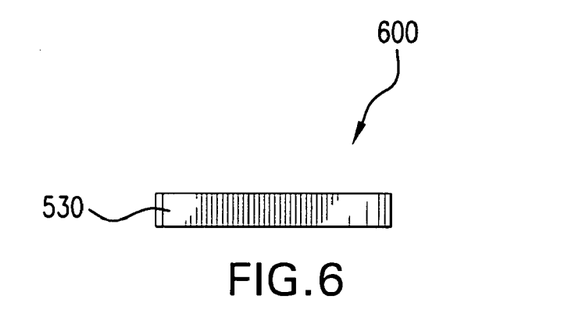
FIG. 6 is a pictorial of an end view of a traditional resection guide.
Figure 7:
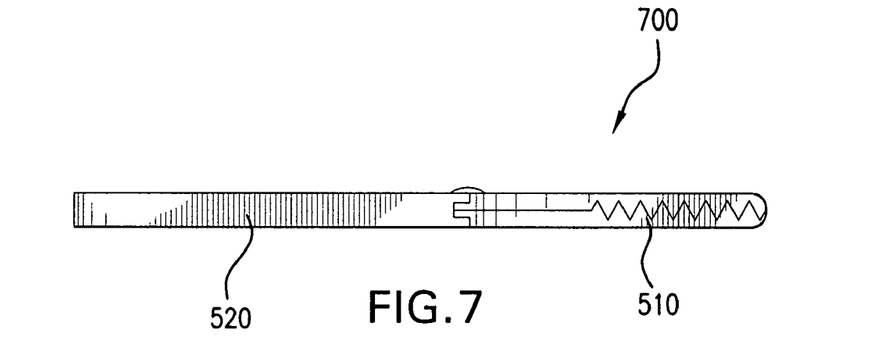
FIG. 7 is a pictorial of a lateral view of a traditional resection guide.

FIG. 5 shows a top view 500 of a traditional patella resector guide having a clamp portion 510, guide handles, 520 and an adjustable bar 530 between the guide handles for fixing the distance between the cradles of the clamp portion. The end view 600 is shown in FIG. 6. Herein, only the side of the bar 530 is seen. The lateral or side view 700 of the traditional resector is shown.

Figure 8:
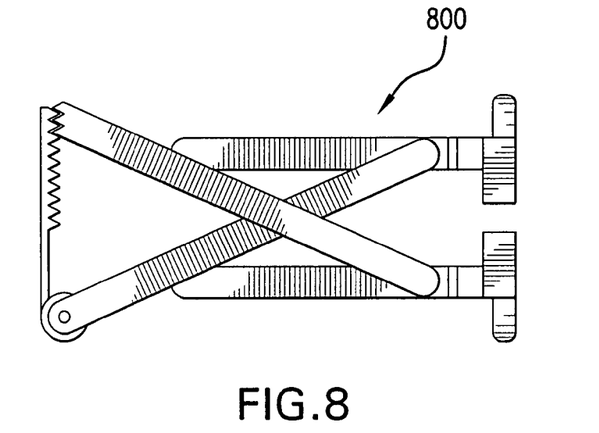
FIG. 8 is a pictorial of a top view of a patella resector in accordance with the present invention.
Figure 9:
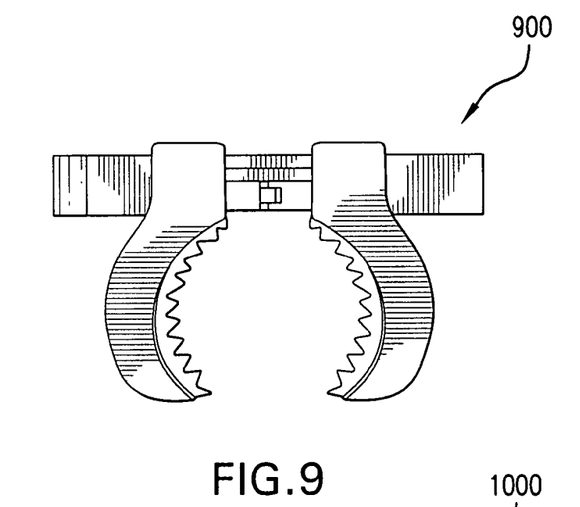
FIG. 9 is a pictorial of an end view of a patella resector in accordance with the present invention.
Figure 10:
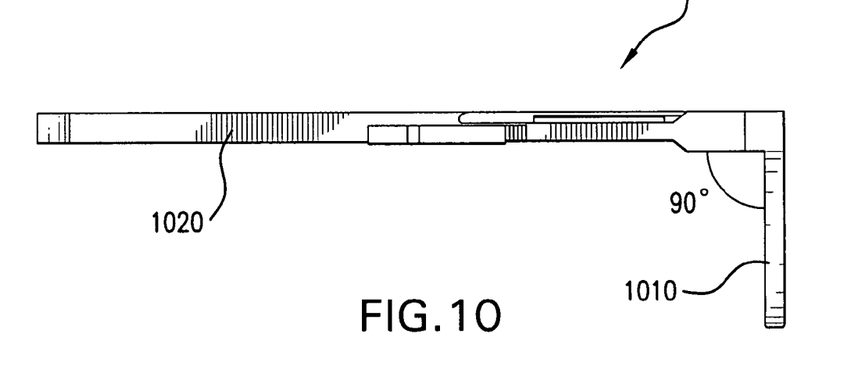
FIG. 10 is a pictorial of a lateral view of a patella resector in accordance with the present invention.

FIGS. 8 through 10 show corresponding views of the patella resection guides presently used in minimally invasive surgery. FIG. 8 is a top down view 800. FIG. 9 is a pictorial of an end view 900. Lateral view 1000 is presented in FIG. 10 wherein the clamp portion 1010 is at a substantially 90 degree angle with the guide handles 1020.

Figure 11:
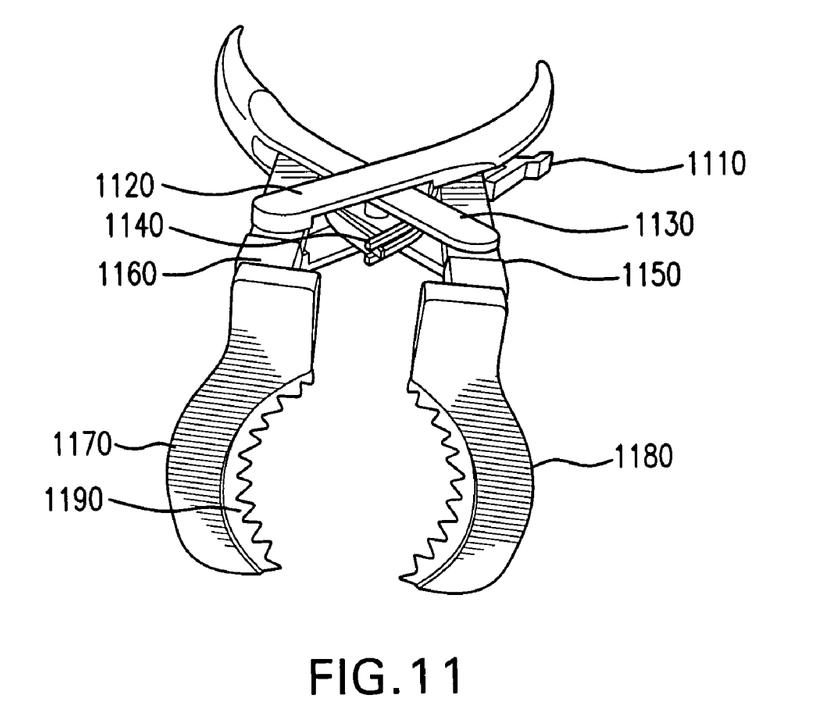
FIG. 11 is a detailed pictorial of a front end view of a patella resector in accordance with the present invention.

FIGS. 11 through 15 depict various views of the patella resector to demonstrate the mechanical arrangement of the resector's parts. FIG. 11 shows a top view 1100 of the patella resector wherein curvilinear gripping handles 1120 and 1130 are shown. The side of gripping handle 1130 includes an adjustable locking means 1110 for fixing the distance between the cradles 1170 and 1180 of the clamp. The curvilinear gripping handles 1120 and 1130 have top and bottom surface wherein an opening is positioned between each top and bottom surface. Gripping handle 1120 is set inside gripping handle 1130 through one of said opening. The gripping handles 1120 and 1130 are pivotally interconnected. The openings of the gripping handles also contain a second pivot 1140, which constitutes an additional portion of the adjustable locking means 1110. The pivot is comprised of two members, each of which is engaged with a corresponding gripping handle.

The gripping handles are connected to ends of stems 1150. The other ends of the stems are connected to a junction 1160 to which the cradles 1170 and 1180 of the clamp are connected. Each cradle has a top flange and a side flange. The side flange is connected to the junction 1160. The top flange contains an inner surface 1190 having teeth for engaging the patient's patella.

Figure 12:
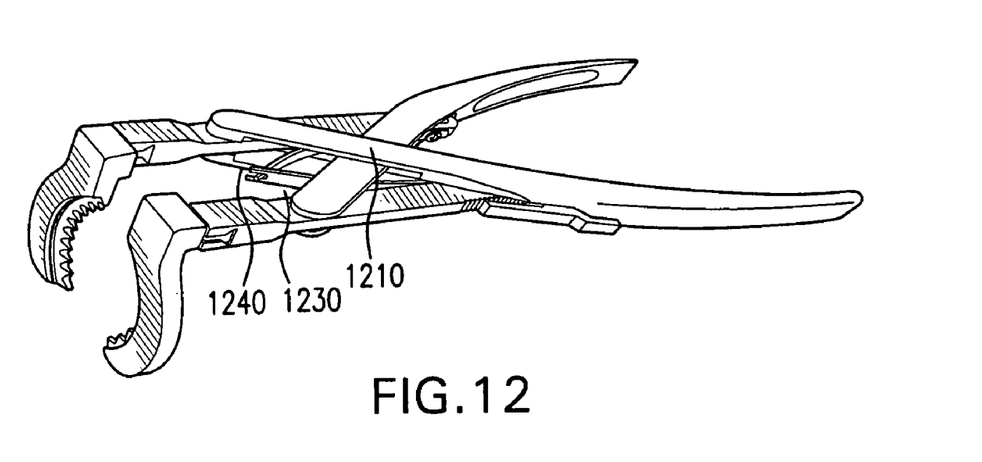
FIG. 12 is a detailed pictorial of a top end view of a patella resector in accordance with the present invention.

A side view 1200 is provided in FIG. 12. This side view shows the seamless top 1210 of the pivotally interconnected members of the gripping handles. The pivot may also be comprised of fastening means such as a screw that will extend through the top and bottom surfaces of the members to form a visible seam. The side of the engaging member 1230 of the second inner pivot is shown. The side of the bottom surface 1240 of stem 1150 is also illustrated.

Figure 13:
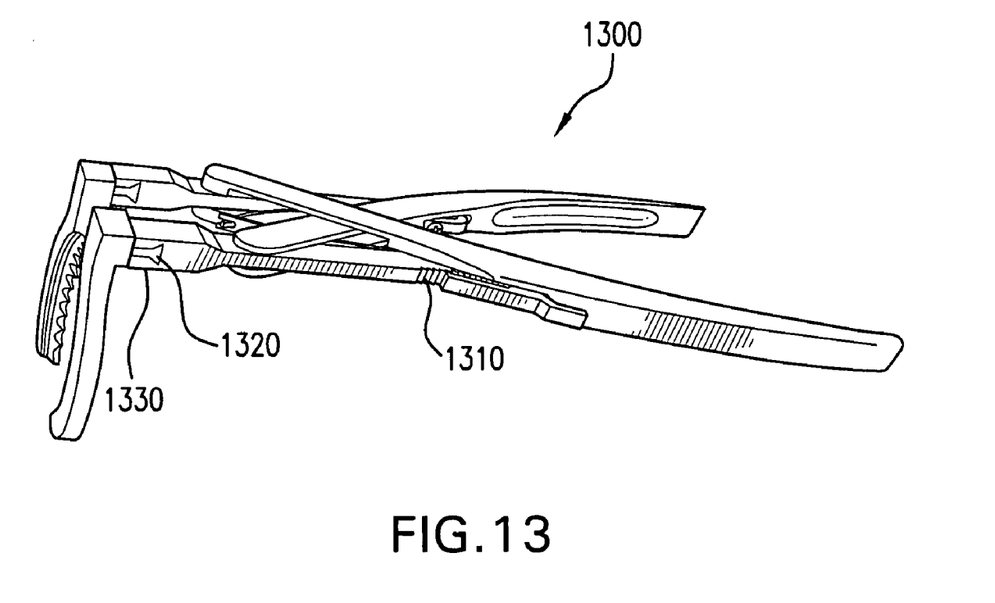
FIG. 13 is a detailed pictorial of a lateral view of a patella resector in accordance with the present invention.

A second pictorial of a side view 1300 of the resector is illustrated in FIG. 13. This view provides a more detailed depiction of the resector's side. The side of gripping member 1130 is shown having a ratcheted surface 1310 for engagement with adjustable locking member 1110. Junction 1260 is comprised of a female receptor 1320 at the end of stem 1150 for receiving the side flange 1330 of the cradle 1180.

Figure 14:
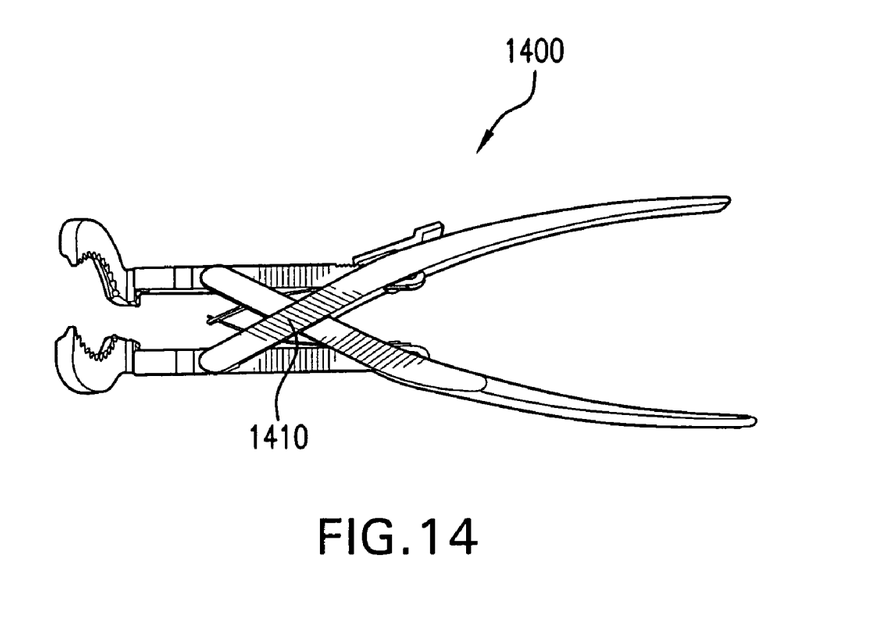
FIG. 14 is a detailed pictorial of an underside view of a patella resector in accordance with the present invention.
Figure 15:
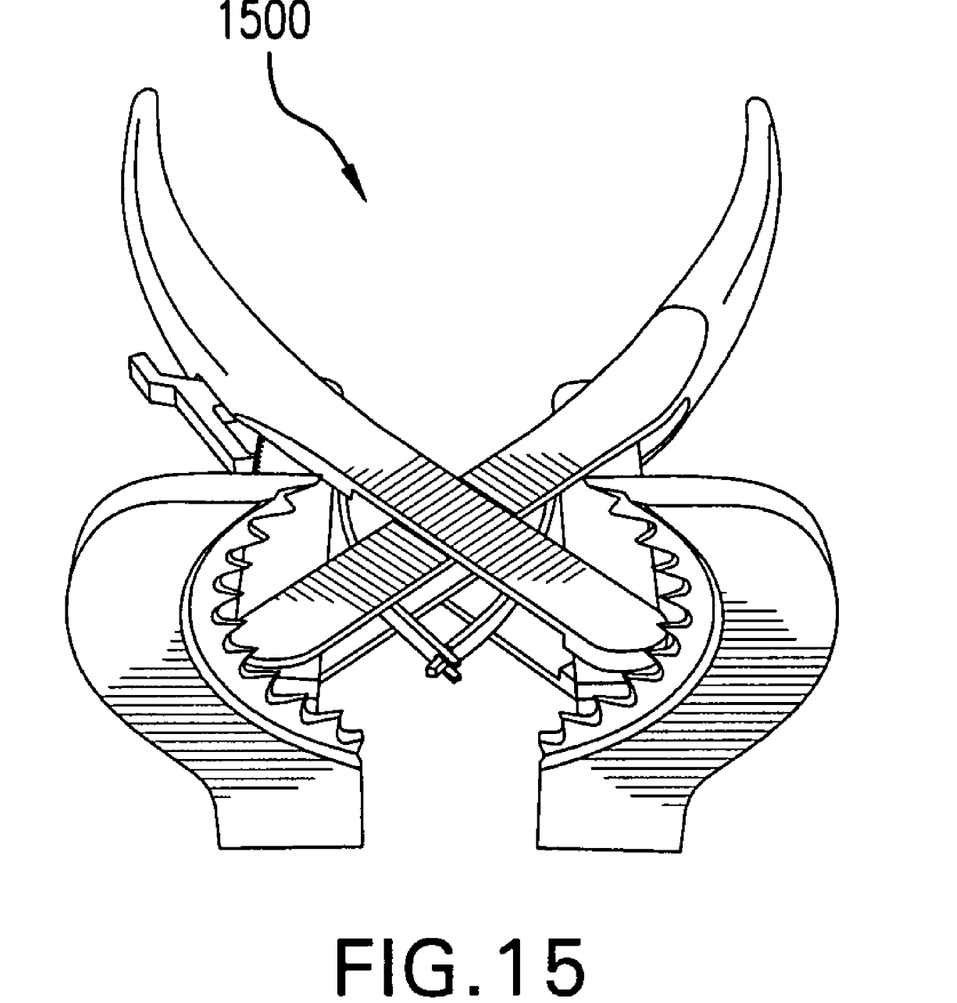
FIG. 15 is a second detailed pictorial of an underside view of a patella resector in accordance with the present invention.

With reference to FIG. 14, a bottom view 1400 of the resector is shown wherein the pivot 1410 is shown with a seamless interconnection of the gripping handles. The bottom view of the pivot may also comprise fastening means which extend through the top and bottom surfaces of each gripping handle. FIG. 15 shows the bottom front or underside front view 1500 of the resector.

Figure 16:
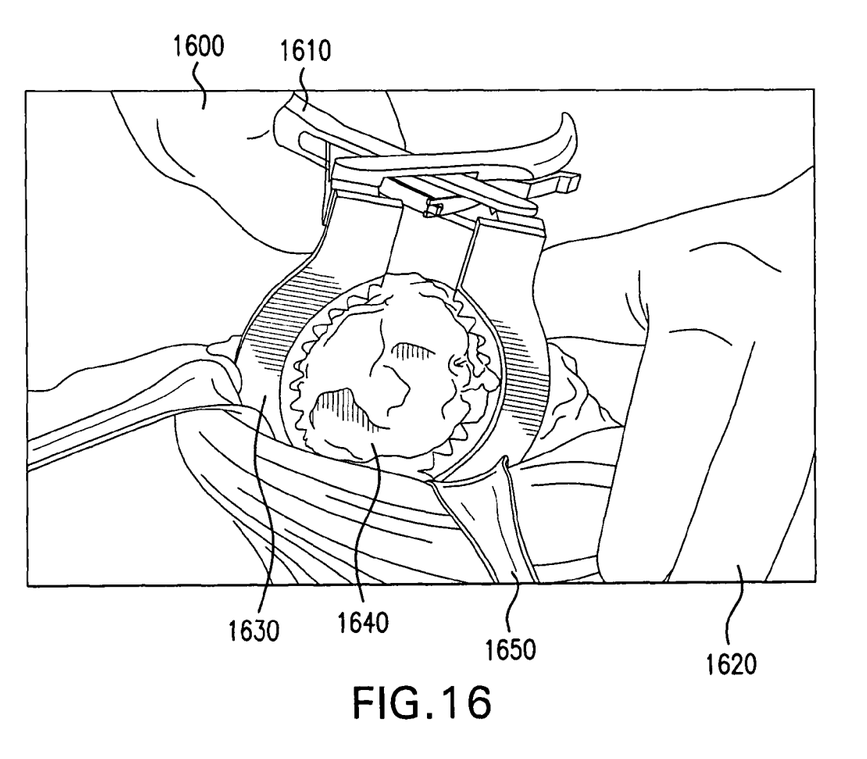
FIG. 16 is a pictorial of a patella resector as applied to a patient's right knee in a surgical procedure in accordance with a method of the present invention.
Figure 17:
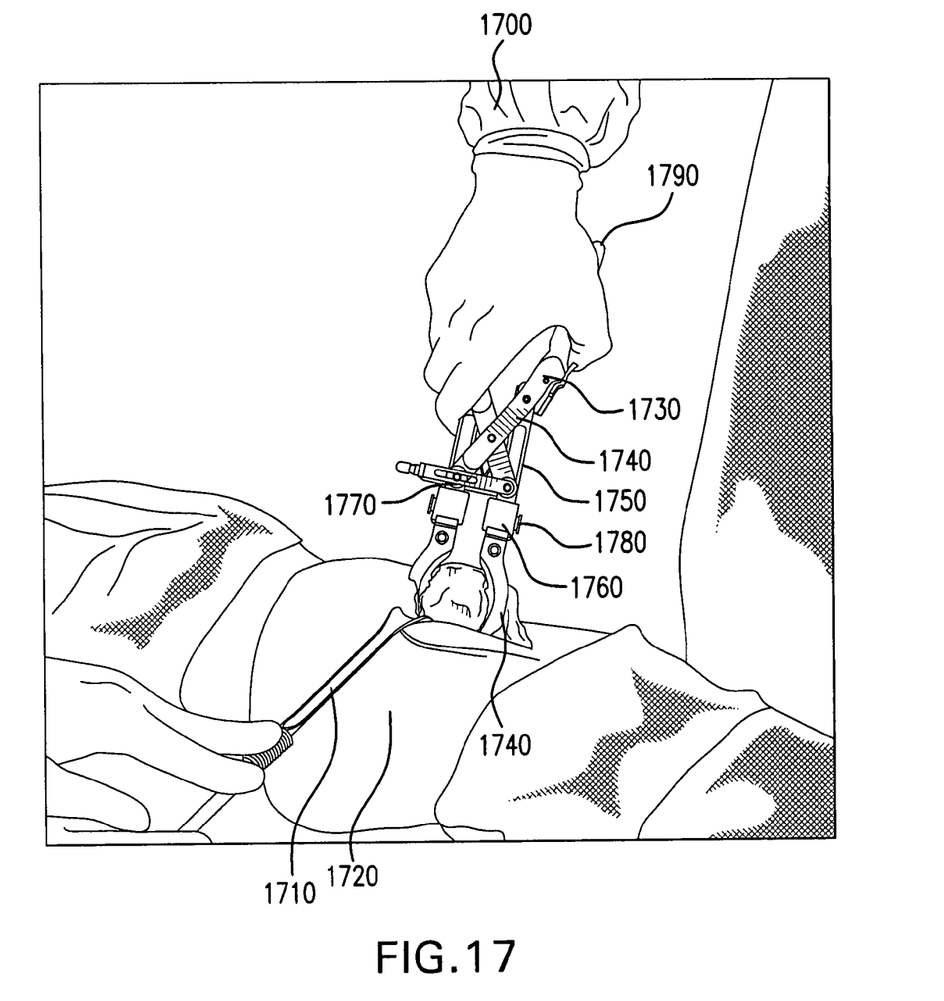
FIG. 17 is a second pictorial of a patella resector as applied to a patient's right knee in a surgical procedure in accordance with a method of the present invention.

FIGS. 16 and 17 depict a method of implementing embodiments of the inventive patella resection guide during minimally invasive surgery in accordance with the present invention. With reference to FIG. 16, surgical tools well known in the art are applied to the surface of a patient's right knee for pulling back the skin to expose the patella of the knee. A surgeon's left hand grasps the patient's right knee for stability, wherein the right hand maneuvers the gripping handles of the patella resection guide. The clamp portion of the patella resection guide applied to the patella, whereby the patella is rotated at a substantially 90 degree angle to expose the undersurface of the patella to the surgeon. The top flange of the clamp is illustrated at a substantially 90 degree angle to the side flange of the clamp.

In FIG. 17, a second embodiment of the patella resection guide of the present invention is depicted as applied by the right hand 1700 of a surgeon to the right knee 1720 of a patient. A typical surgical tool 1710 well known in the prior art is used to pull back the skin of the right knee 1720 to expose the patella. The second embodiment of the patella resection guide comprises a pair of gripping handles 1730 wherein the end of the handles distal to the surgeon's hand are connected to intersecting bars 1790 having a top surface and bottom surface wherein the surfaces of each gripping intersecting bar contains screws for securing top and bottom portions of the gripping handles to one another and to corresponding junctions of the patella resection guide. One such junction is depicted at the crossing point of the gripping handles at ends distal to the surgeon's right hand. The gripping handles may be linear or curvilinear. Proximal to each gripping handle 1730 is a stem 1750 comprised of parallel bars which are connected to the gripping handles and intersecting bars at one end and to a junction 1760 at the other end of the parallel bars. The stems 1750 are parallel bars are connected to junction 1760 via screws 1780. Adjoined to the bottom of junction 1760 and proximal to the crossing point of the gripping handles is an adjustable locking means 1770 for adjustably engaging the stem of the right stem to the left stem at a fixed distance. The clamp is positioned at a substantially 180 degree angle to junction 1760.

While various embodiments of the present invention have been described herein, it should be understood that various changes, adaptations, and modifications of the appending claims may be made without departing from the spirit of the invention and the scope

The invention claimed is:

1. A patella resection guide for minimally invasive surgery, said patella resection guide comprising:
   first and second gripping handles having corresponding first and second pivotally interconnected crossover members at distal ends of each of said first and second gripping handles;
   an opening in each of said first and second pivotally interconnecting crossover members wherein one of said first and second pivotally interconnecting crossover members is positioned inside another of said first and second pivotally interconnecting crossover members;
   first and second stems, each of said first and second stems comprising:
      a proximal end connected to each of said first and second gripping handles and each of said first and second pivotally interconnected crossover members, wherein said first and second pivotally interconnected crossover members are intertwined at a crossing point and are adjoined by a fastening means to said first and second stems, and
   a clamp, comprising:
      first and second cradles;
      a first plane containing bottom surfaces of said first and second cradles of said clamp positioned at a substantially 90 degree angle with respect to a second plane containing bottom surfaces of said first and second gripping handles; and
      adjustable locking means for fixing a distance between said first and second cradles of said clamp.

2. The patella resection guide of claim 1, wherein said clamp comprises a pair of top flanges and first and second side flanges; a female receptor on said distal end of each of said first and second stems receiving said first and second side flanges; each of said top flanges comprising a curved inner surface contoured to a shape of a patella.

3. The patella resection guide of claim 2, wherein each of said top flanges comprises teeth for gripping the patella within said clamp.

4. The patella resection guide of claim 1, wherein said first and second gripping handles are curvilinear.

5. The patella resection guide of claim 1, wherein said fastening means is a screw.

6. The patella resection guide of claim 1, wherein said adjustable locking means comprises a ratcheted surface on a side of one of said first and second stems and an adjustable locking member attached to said one of said first and second gripping handles and positioned for engagement with said ratcheted surface.

7. The patella resection guide of claim 1, wherein said first and second stems are each comprised of a solid bar.

8. The patella resection guide of claim 1, wherein said first and second stems are comprised of parallel bars.

9. A method for resecting a patella in minimally invasive surgery, said method comprising:
- surgically exposing the patella and adjacent ligament and tendon structures;
- providing a patella resection guide having first and second gripping handles having corresponding first and second pivotally interconnected crossover members at distal ends of each of said first and second gripping handles; an opening in each of said first and second pivotally interconnecting crossover members wherein one of said first and second pivotally interconnecting crossover members is positioned inside another of said first and second pivotally interconnecting crossover members; first and second stems, each of said first and second stems comprising a proximal end connected to each of said first and second gripping handles and each of said first and second pivotally interconnected crossover members, wherein said first and second pivotally interconnected crossover members are intertwined at a crossing point and are adjoined by a fastening means to said first and second stems; a clamp comprising first and second cradles, wherein said first and second cradles each comprise a top flange; a first plane containing bottom surfaces of said first and second cradles of said clamp positioned at a substantially 90 degree angle with respect to a second plane containing bottom surfaces of said first and second gripping handles; and adjustable locking means for fixing a distance between said first and second cradles of said clamp;
- engaging said adjustable locking means;
- applying the cradles to the patella; and
- rotating the patella to expose an undersurface of the patella to a user of the patella resection guide.

10. The method of claim 9, wherein said clamp comprises a pair of top flanges and first and second side flanges; a female receptor on said distal end of each of said first and second stems receiving said first and second side flanges; each of said top flanges comprising a curved inner surface contoured to a shape of a patella.

11. The method of claim 10, wherein each of said top flanges comprises teeth for gripping the patella within said clamp.

12. The method of claim 9, wherein said first and second gripping handles are curvilinear.

13. The method of claim 9, wherein said fastening means is a screw.

14. The method of claim 9, wherein said adjustable locking means comprises a ratcheted surface on a side of one of said first and second gripping handles and an adjustable locking member attached to said one of said first and second gripping handles and positioned for engagement with said ratcheted surface.

15. The method of claim 9, wherein said adjustable locking means is a latching mechanism.

16. The method of claim 9, wherein said first and second stems are comprised of parallel bars.

17. A patella resection guide for minimally invasive surgery, said patella section guide comprising:
- first and second gripping handles;
- first and second pivotally interconnected crossover members adjoined to said first and second gripping handles;
- first and second stems, each connected to each of said first and second gripping handles and each of said first and second pivotally interconnected crossover members, wherein each of said first and second pivotally interconnected crossover members are intertwined at a crossing point and are adjoined by fastening means to said first and second stems;
- a clamp, comprising:
  - first and second cradles, wherein said cradles comprise a pair of top flanges; and
  - first and second side flanges, wherein a female receptor on a distal end of each of said first and second stems receives said first and second side flanges respectively, and wherein a first plane containing bottom surfaces of said first and second cradles of said clamp is positioned at a substantially 90 degree angle to a second plane containing bottom surfaces of said first and second gripping handles; and
- adjustable locking means for fixing a distance between said first and second cradles of said clamp.

18. The patella resection guide of claim 17, wherein said first and second gripping handles are curvilinear.

19. The patella resection guide of claim 17, wherein said top flanges comprise a curved inner surface contoured to a shape of a patella.

20. The patella resection guide of claim 17, wherein said top flanges comprise a curved inner surface contoured to a shape of a patella and having teeth for gripping the patella within said clamp.

21. The patella resection guide of claim 17, wherein said fastening means is a screw.

22. The patella resection guide of claim 17, wherein said adjustable locking means is a latching mechanism.

23. A method for resecting a patella in minimally invasive surgery, said method comprising:
- surgically exposing a top surface of a patella of a patient's knee for application of a patella resection guide;
- securing a pair of top flanges of a clamp of said patella resection guide to the patella, wherein a first plane containing bottom surfaces of first and second cradles of said clamp is positioned at a substantially 90 degree angle to a second plane containing bottom surfaces of first and second gripping handles of said clamp;
  - wherein said patella resection guide further comprises first and second pivotally interconnected crossover members, first and second stems, each connected to each of said first and second gripping handles and each of said first and second pivotally interconnected crossover members, wherein said first and second pivotally interconnected crossover members are adjoined by fastening means to said first and second stems and wherein said first and second stems are further adjoined by a fastening means to said clamp; and adjustable locking means for fixing a distance between said first and second cradles of said clamp;
- engaging said adjustable locking means so as to maintain the patella in a fixed position; and
- rotating the patella to expose an undersurface of the patella to a user of said patella resection guide; and
- resecting the patella.

24. The method of claim 23, wherein said top flanges comprise a curved inner surface contoured to a shape of a patella.

25. The method of claim 23, wherein said first and second gripping handles are curvilinear.

26. The method of claim 23, wherein said top flange comprises a curved inner surface contoured to a shape of a patella and having teeth for gripping the patella within said clamp.

27. The method of claim 23, wherein said fastening means is a screw.

28. The method of claim 23, wherein said adjustable locking means is a latching mechanism.

29. The method of claim 23, wherein said first and second stems are comprised of parallel bars.

* * * * *